United States Patent [19]
Cantrell

[11] Patent Number: 5,591,121
[45] Date of Patent: Jan. 7, 1997

[54] LIMB SPLINT AND RESTRAINT

[76] Inventor: Mary A. Cantrell, 3282 Kepley Rd., Georgetown, Ind. 47122

[21] Appl. No.: 386,003

[22] Filed: Feb. 9, 1995

[51] Int. Cl.$^6$ ........................................................ A61F 5/00
[52] U.S. Cl. .................................... 602/5; 602/20; 602/21
[58] Field of Search .................................... 602/5, 20, 23, 602/25, 26, 9, 21, 22; 128/869, 877, 878

[56] References Cited

U.S. PATENT DOCUMENTS

| | | |
|---|---|---|
| 2,606,554 | 8/1952 | Simon . |
| 2,933,083 | 4/1960 | Kozdas ........................................ 602/5 |
| 3,010,452 | 11/1961 | Smith . |
| 3,115,132 | 12/1963 | Hill . |
| 3,776,225 | 12/1973 | Lonardo . |
| 3,804,084 | 4/1974 | Lehman .................................... 602/26 |
| 4,070,027 | 1/1978 | Kifferstein . |
| 4,078,560 | 3/1978 | Hill . |
| 4,142,522 | 3/1979 | Hill ........................................ 602/20 X |
| 4,254,766 | 3/1981 | Kordis . |
| 4,481,942 | 11/1984 | Duncan . |
| 4,492,225 | 1/1985 | Picolet et al. ............................. 602/20 |
| 4,503,849 | 3/1985 | Morgan . |
| 4,829,992 | 5/1989 | Cilladi . |
| 4,941,479 | 7/1990 | Russell . |
| 4,941,480 | 7/1990 | McLean . |
| 5,248,292 | 9/1993 | Holland . |
| 5,277,954 | 1/1994 | Carpenter et al. ....................... 428/71 |

OTHER PUBLICATIONS

Smith and Nephew Rolyan Rehabilitation Products 1995 Catalog Urias® Air Splints, 1995, p. 101.

Primary Examiner—Richard J. Apley
Assistant Examiner—Kim M. Lee
Attorney, Agent, or Firm—Wheat, Camoriano, Smith & Beres, PLC

[57] ABSTRACT

A device for maintaining limb extension and restraint for children and adults. It comprises a series of longitudinal pockets sewn into a machine launderable, soft, non-allergenic fabric. The pockets can be opened and closed using hook and loop fasteners to remove or replace reinforcing members. The pockets contain elongated resilient foam reinforcing made of a cross-link polyethylene foam, for softness, absorption and laundering by machine. The foam reinforcing is made with a sufficient diameter so as to increase its strength against limb flexion. The foam reinforcing is cylindrical in shape and situated in a series of longitudinal rows that lie parallel to the limb when the splint is worn. Because of its configuration of longitudinal reinforcing members, it provides air flow between the limb and splint through a series of longitudinal openings between the structural members that provides comfort to the patient. The splint can be modified to include an open area for skin ulcerations at the inside of elbows or behind the knees. The modification utilizes longitudinal padded rigid reinforcing, made of a low temperature thermal plastic, and placed parallel to the length of the limb around that part of the arm not lying in the open area, for structural support. The splint can also be modified to contain fully padded rigid reinforcing members that are moldable to the patient's greatest angle of limb extension, be it fully or partially extended, and maintain the limb at its angle of extension.

6 Claims, 6 Drawing Sheets

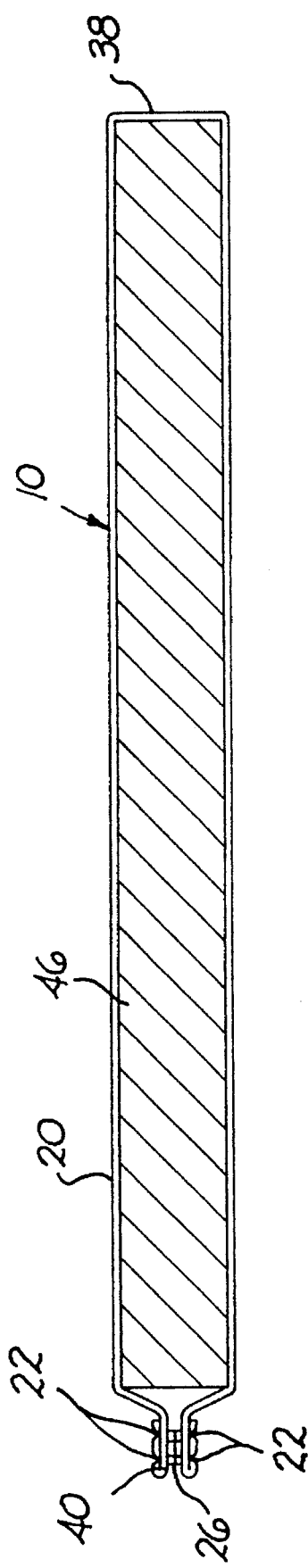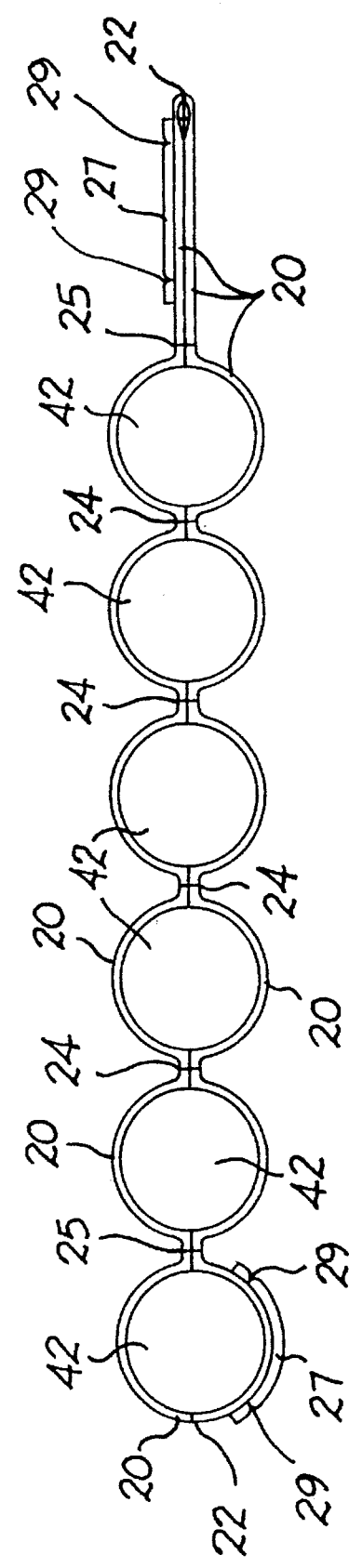
FIG. 11
FIG. 12

LIMB SPLINT AND RESTRAINT

BACKGROUND—FIELD OF INVENTION

This invention is in the field of medical equipment and specifically relates to elbow or knee splints for children and adults.

BACKGROUND—DESCRIPTION OF PRIOR ART

Presently, limb splints and restraints are used to keep a limb extended so that the limb doesn't lose it's range of motion due to too much flexion. Other reasons for the use of limb splints are to facilitate intravenous injections and feedings, to restrict movement of elbows or knees, to keep a patient from biting their arms and hands, and to accomplish the progressive extension of a limb. It is also desirable that the limb splint be comfortable, soft, non-allergenic and be machine washable.

One prior art, shown by U.S. Pat. No. 4,481,942, to Duncan, Sep. 4, 1979, is a unitary flexible plastic sheet with a washable fabric covering permanently sewed together. This prior art is intended to be machine laundered or sterilized without the removal of the reinforcing member and protect the patients skin from direct contact with foam or other plastic material thereby preventing skin irritation and abrasion. However, it prohibits air flow between the splint and the limb, causing perspiration and discomfort. Furthermore, the plastic sheet does not absorb the perspiration. Another disadvantage of the splint is that, should the flexible plastic sheet lose its limb extension supporting ability the whole splint must be discarded, not just the plastic sheet.

Another prior art, shown by U.S. Pat. No. 2,606,554, to Simon, Sep. 17, 1949, can also be laundered but after removal of the reinforcing sheet member. However, it also prohibits air flow and does not absorb perspiration.

Air splints are another prior art made to extend the limb of a patient. They are not launderable by machine. They are hot and non-absorbing. Their zippers break and they pop easily. Patients who bite are able to bite the air splints and pop them.

Other limb splints are also made of a unitary resilient reinforcing sheet material as shown in U.S. Pat. No. 4,941,480, to McLean, Jun. 7, 1989, U.S. Pat. No. 4,070,027, to Kifferstein, Jul. 19, 1976 and U.S. Pat. No. 4,829,992, to Cilladi, Oct. 1, 1987. However, they too are non-absorbing and not machine launderable.

Much of the prior art requires the limb splint reinforcing to be a unitary rigid plastic material as shown in U.S. Pat. No. 4,941,479, to Russell, Sep. 5, 1989, U.S. Pat. No. 4,078,560, to Hill, Aug. 4, 1976, U.S. Pat. No. 4,142,522, to Hill, Sep. 19, 1977, U.S. Pat. No. 3,010,452, to Smith, Mar. 9, 1960, U.S. Pat. No. 3,115,132, to Hill, Oct. 23, 1961, U.S. Pat. No. 3,776,225, to Lonardo, Jul. 12, 1971, U.S. Pat. No. 4,254,766, to Kordis, Jul. 12, 1979, U.S. Pat. No. 4,503,849, to Morgan, Sep. 16, 1982, and U.S. Pat. No. 4,941,479, to Russell, Jul. 17, 1990. However, the rigid structural support material is exposed in each case. This allows contact between skin and splint causing skin irritation. These splints are also non-absorbing and not launderable by machine.

There are no prior inventions that provide a group of individual, resilient, absorbing, machine washable and dryable, structural reinforcing members encased in fabric.

OBJECTS AND ADVANTAGES

Accordingly, several objects and advantages of the present invention are:
(a) to provide a limb splint that maintains it's structural resistance to limb extension by utilizing a series of cylindrical longitudinal resilient reinforcing members situated parallel to the length of the limb around the limb. These provide greater strength against bending because they have a greater section modulus than a single thin sheet of flexible reinforcing.
(b) to provide a limb splint with air flow between the limb and the splint through a series of longitudinal openings between the structural reinforcing members of the splint.
(c) to provide a soft, absorbing, comfortable, non-allergenic and machine launderable fabric covered limb splint.
(d) to provide a limb splint with removable or replaceable reinforcing members.
(e) to provide a splint that restricts the movement of elbows or knees and keeps the patient from hitting or biting himself/herself.
(f) to provide a splint that is inexpensive to manufacture in custom or standard sizes.
(g) to provide a splint which can be modified to include an open area for skin ulcerations at the inside of elbows or behind the knees and continuing with longitudinal padded rigid reinforcing members parallel to the length of the limb around the rest of the limb for structural support.
(h) to provide a splint that can be modified to contain fully padded rigid reinforcing members that are moldable to the patient's greatest angle of limb extension, be it fully extended or partially extended, and that maintain the limb at its angle of extension.

Further objects and advantages will become apparent from a consideration of the ensuing description and drawings.

DRAWING FIGURES

FIG. 11 is an enlarged cross-sectional view taken on line 11—11 of FIG. 10.

FIG. 12 is an enlarged cross-sectional view taken on line 12—12 of FIG. 10.

Figure 1:
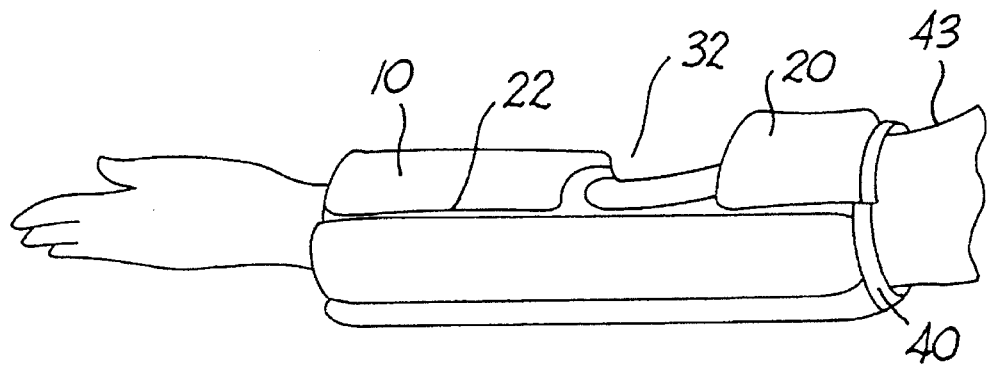
FIG. 1 is an illustration of the right side view of the modified limb splint and restraint device worn on a fully extended arm showing an overlap of layers.

REFERENCE NUMERALS IN DRAWINGS 20 fabric
22 seam
24 stitching
26 hook and loop fastener
28 rigid reinforcing rod
30 hollow cylindrical foam reinforcing
32 opening
34 foam pad
36 modified limb splint and restraint
38 fold
40 hook and loop fastened seam
42 pockets
44 limb splint and restraint
46 cylindrical resilient foam reinforcing

DESCRIPTION AND OPERATION OF INVENTION—FIGS. 1 TO 12

Figure 10:
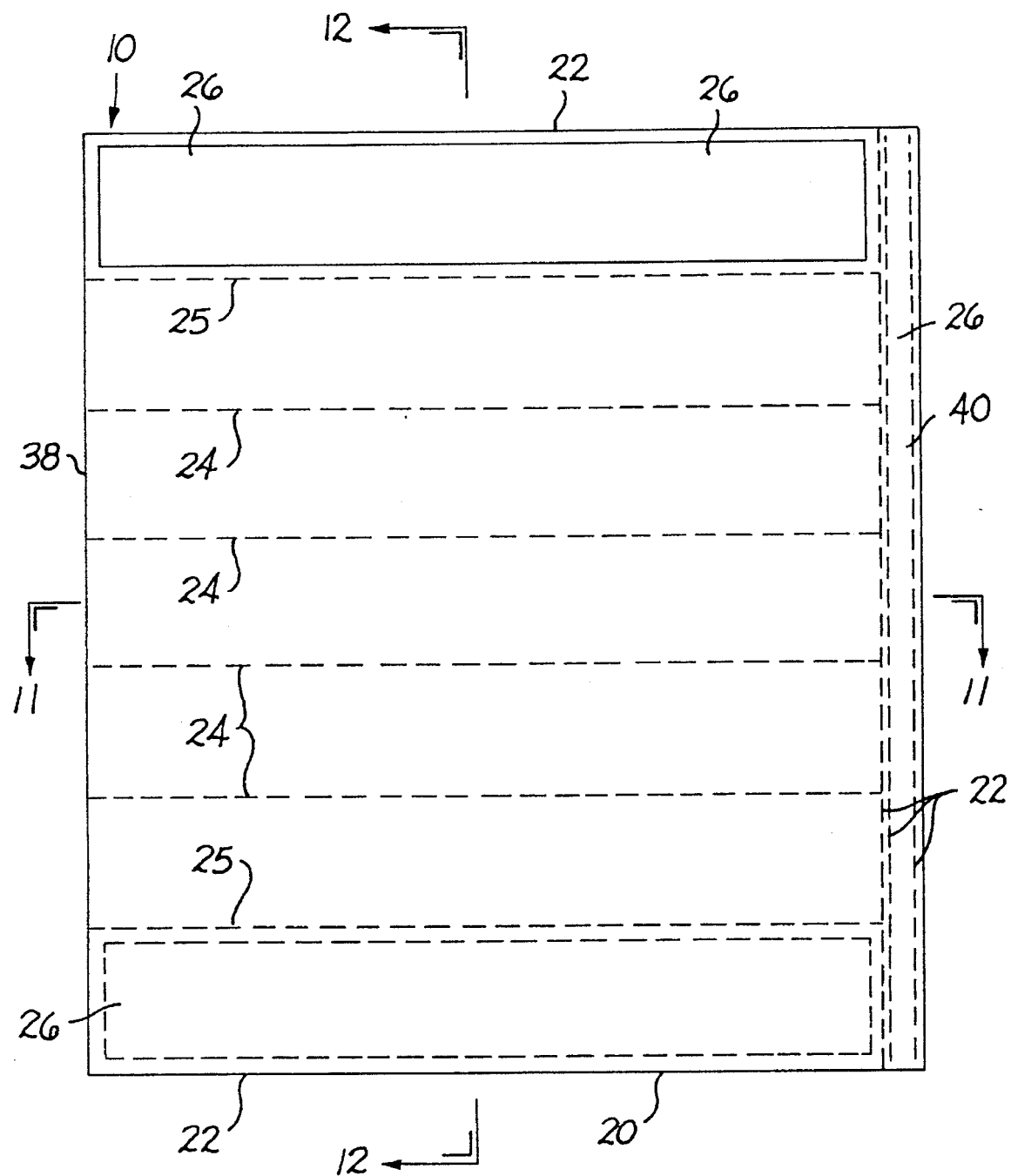
FIG. 10 is a plan view of the limb splint and restraint device lying flat prior to being placed around a limb in a generally tubular manner and utilizing unbent resilient reinforcing.

FIG. 10 shows a plan view of the limb splint and restraint 44 prior to being placed around a limb.

Limb splint 44 comprises a machine washable and dryable, non-allergenic, soft fabric 20 cut on a fold 38 in a generally rectangular shape. Next, the edges opposite the fold are finished by turning under 0.64 cm. towards the wrong side of fabric 20 and then turned under another 0.64 cm. towards the wrong side of fabric 20 and stitched. The edges are turned under 2.54 cm. more towards wrong side of fabric 20 and hemmed. FIGS. 5, 10, 11 and 12 show complementing hook and loop fasteners 26 are sewn along the length of both edges leaving 1.27 cm. at each end for seams 22. The hook and loop fasteners 26 can be 1.27 cm., 1.59 cm., 1.90 cm. or 2.54 cm. wide. These hook and loop fastened edges are now referred to as the hook and loop fastened seam 40.

Prior to sewing the fabric 20 together at seams 22, hook and loop fasteners 26 of sufficient width are sewn parallel to the seam 22 edges leaving at least 1.27 cm. seam 22 allowance from fabric 20 edges. The complementing hook and loop fasteners 26 are sewn on the top right and bottom left of limb splint 44. That is, the hook portion of fastener is on top right and loop portion of fastener is on bottom left or vice versa.

Next, fabric 20 is sewn together at side seams 22 as shown in FIGS. 10 and 12. Subsequently, a series of rows of stitching 24 are sewn longitudinally parallel with the side seams 22 of limb splint 44 from the fold 38 to the hook and loop fastened seam 40. Stitching 24 forms a series of pockets 42, 2.54 cm. to 10.16 cm. wide.

Limb splint 44 comprises all cylindrical resilient foam reinforcing 46, as shown in FIGS. 11 and 12. The foam reinforcing 46 is inserted through the hook and loop fastened seam 40, shown cross sectioned in FIG. 5 and 11. The foam reinforcing provides the limb splint 44 the strength to resist bending of the limb at the elbow or knee and keep the limb fully extended.

The cylindrical resilient foam reinforcing 46, as shown in FIGS. 11 and 12, is made of solid cylindrical cross-link polyethylene foam or 0.64 cm. thick cross-link polyethylene sheet rolled into a cylinder, or similar. Resilient foam reinforcing 46 should be made a sufficient thickness to support the limb extension of a patient depending on the patients size and strength and on the reinforcing material chosen. The resilient foam reinforcing 46 absorbs perspiration and is completely machine launderable.

Further, the resilient foam reinforcing 46 is inserted into the pockets 42, as shown in FIGS. 9, 10, 11 and 12. One outer pocket may be left unstuffed to be used as a securing overlap. Secure with hook and loop fastened seam 40.

Figure 9:
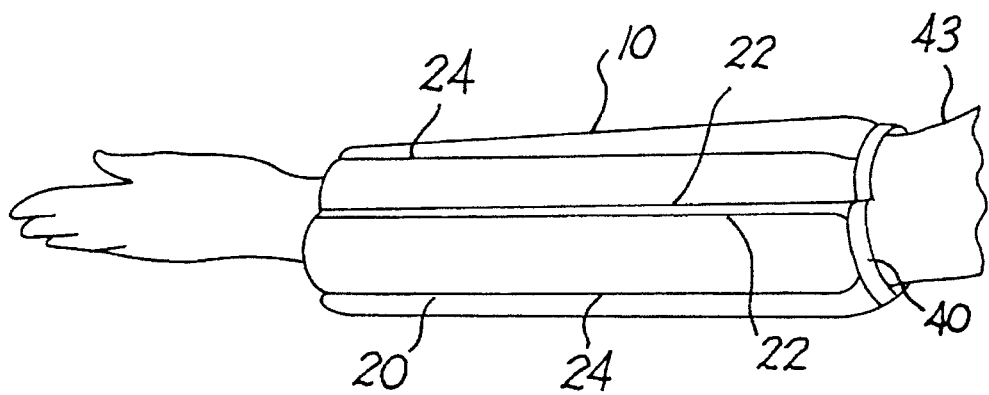
FIG. 9 is an illustration of the limb splint and restraint device worn on a fully extended arm.

Finally, the limb splint 44 is folded about the limb in a generally tubular form as shown in FIG. 9. Hook and loop fasteners 26 at the sides of limb splint 44 secure it about the limb. Continuous rows of resilient foam reinforcing 46, or another choice of reinforcing, are situated parallel with the length of the limb all around the limb.

Figure 3:
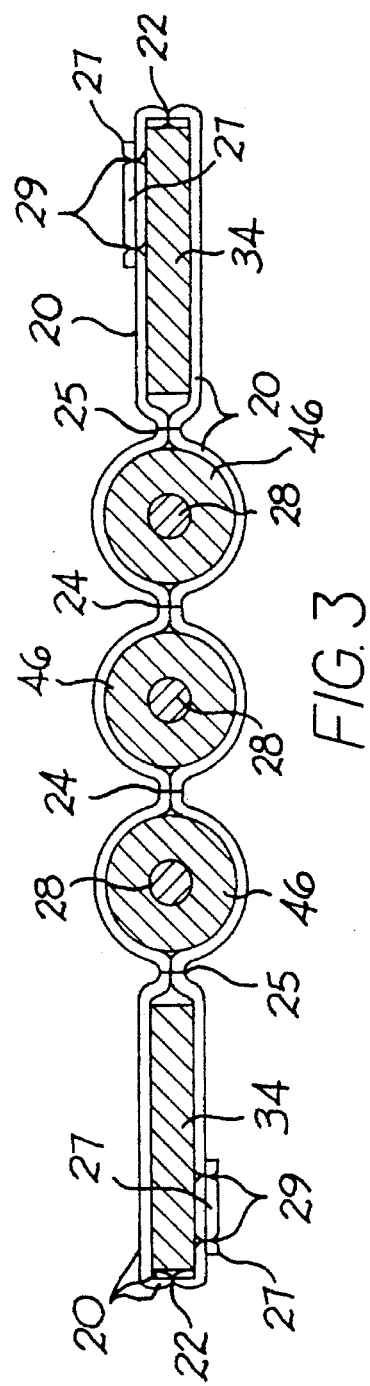
FIG. 3 is an enlarged cross-sectional view taken on line 3—3 of FIG. 8.
Figure 4:
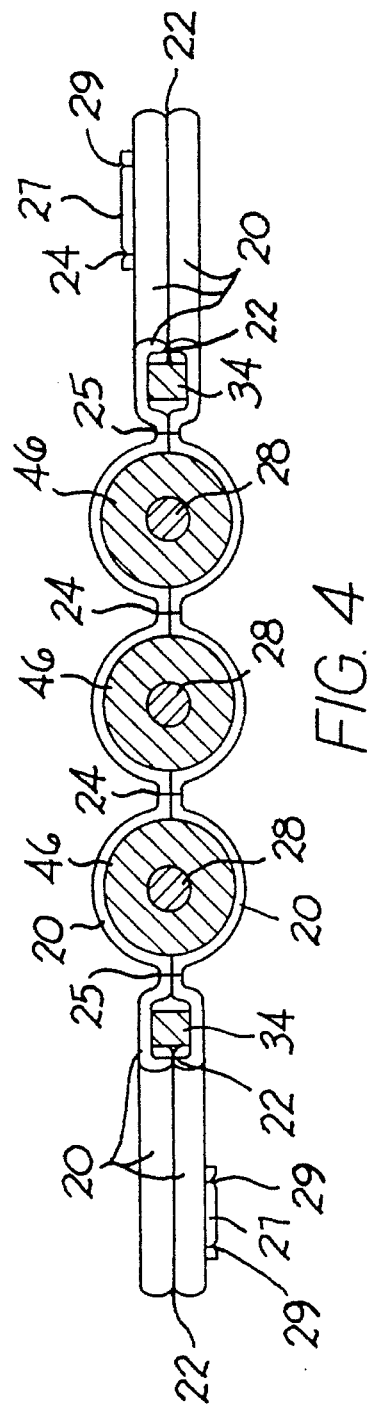
FIG. 4 is an enlarged cross-sectional view taken on line 4—4 of FIG. 8.

The parallel cylinders of reinforcing have spaces between them, due to their circular shape, to allow for air flow between the limb and limb splint 44 or 36, as shown in FIGS. 3, 4, and 12.

Figure 8:
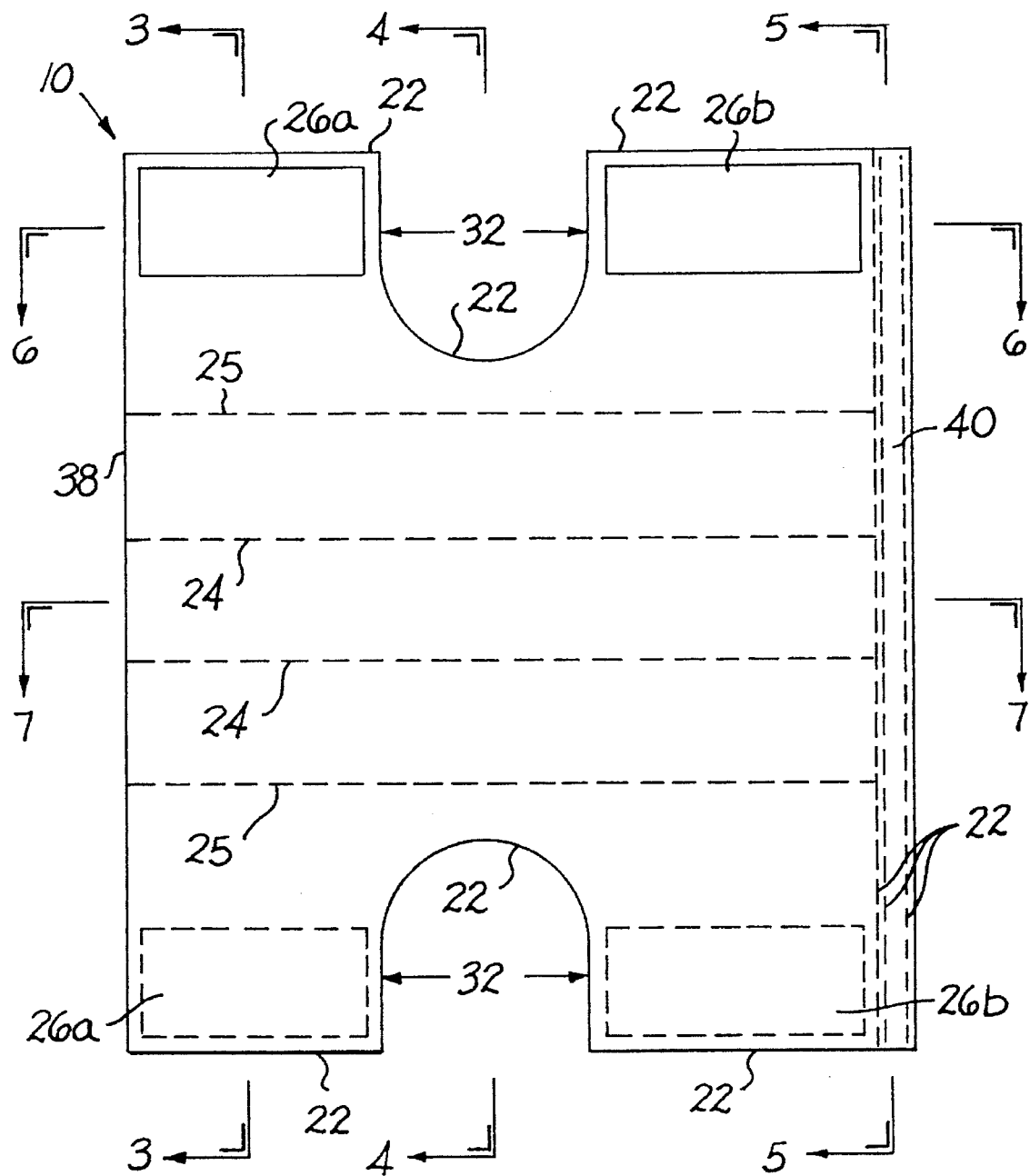
FIG. 8 is a plan view of the modified limb splint and restraint device lying flat prior to being placed around a limb in a generally tubular manner and utilizing unbent or unmolded rigid reinforcing.

FIG. 8 shows a plan view of the modified limb splint and restraint device 36 lying flat prior to being placed around a limb. The limb splint 36 includes an opening for skin ulcerations inside the elbow or behind the knee.

Figure 5:
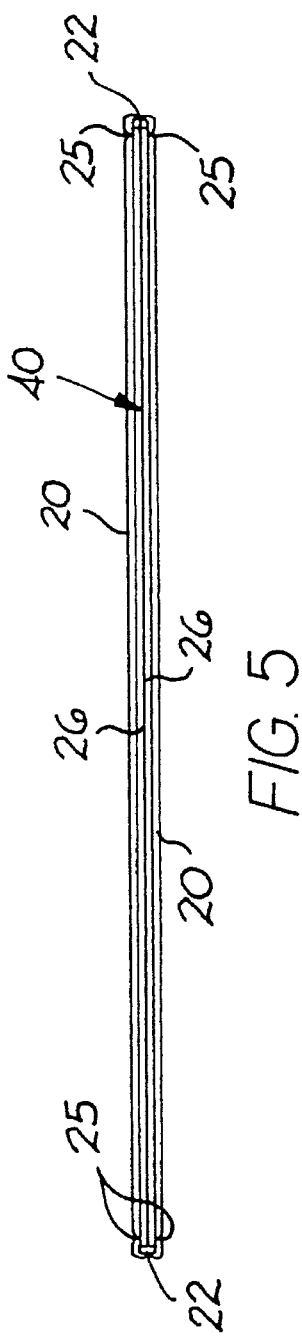
FIG. 5 is an enlarged cross-sectional view taken on line 5—5 of FIG. 8.
Figure 6:
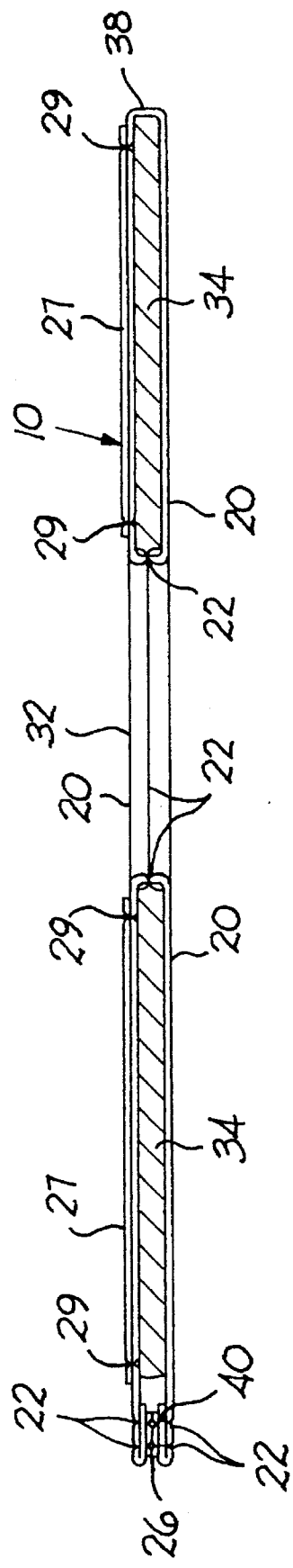
FIG. 6 is an enlarged cross-sectional view taken on line 6—6 of FIG. 8.
Figure 7:
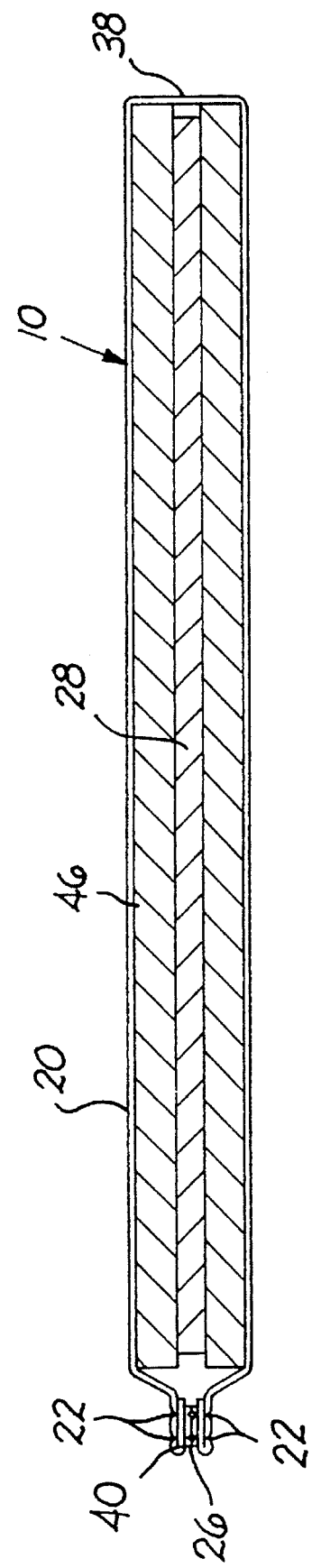
FIG. 7 is an enlarged cross-sectional view taken on line 7—7 of FIG. 8.

Limb splint 36 comprises a machine washable and dryable, non-allergenic, soft fabric 20 cut on a fold 38 in a generally rectangular shape with semi-circular extended openings 32. Openings 32 are a little off center of the shorter sides of limb splint 36. In FIG. 8, a fold 38 is shown to be on one of the longer sides of limb splint 36. Next, the edges opposite the fold are finished by turning under 0.64 cm. towards wrong side of fabric 20 and then another 0.64 cm. towards the wrong side of fabric 20 and stitching. The finished edges are folded over 2.54 cm. more towards wrong side of fabric 20 to hem. FIGS. 5, 6, and 7 show complementing hook and loop fasteners 26 are sewn along the length of both edges leaving 1.27 cm. at each end for seams 22. The hook and loop fastener 26 can be 1.27 cm., 1.59 cm., 1.90 cm. or 2.54 cm. wide. This edge is now referred to as the hook and loop fastened seam 40.

Next, hook and loop fasteners 26 of sufficient width are sewn on either side of openings 32 parallel to and along most of the length of the limb splints 36 shorter sides, as shown in FIGS. 3, 4, 6, and 8. The complementing hook and loop fasteners 26 are sewn on the top right and bottom left of limb splint 36, that is hook portion of fastener is on top right and loop portion is on bottom left or vice versa.

Next, fabric 20 is sewn together along both shorter sides, following cut-outs for openings 32, with seams 22, as shown in FIGS. 3, 4, and 5 cross-sections.

FIGS. 3, 4, and 6 show limb splint 36 comprises foam padding 34 between two layers of fabric 20. Subsequently, foam padding 34 is cut to fit and placed into the fabric 20 after the side seams 22 are sewn but prior to sewing the first row of stitching 24 for pockets 42. The foam padding is 1.27 cm. to 2.54 cm. thick soft, polyethylene foam.

Next, a series of rows of stitching 24 are sewn longitudinally parallel with the shorter sides of the limb splint 36 from the fold 38 to hook and loop fastened seam 40. Stitching 24 forms a series of pockets 42, 2.54 cm. to 10.2 cm. wide.

The hook and loop fastened seam 40, referred to previously and shown cross-sectioned in FIGS. 5, 6, and 7 permits the easy removal for washing or replacement of cylindrical rigid reinforcing rods 28 and hollow cylindrical foam reinforcing 30 into pockets 42.

Limb splint 36 comprises rigid reinforcing rods 28 surrounded by foam reinforcing 30 inside pockets 42, as shown cross-sectioned in FIGS. 3, 4, and 7. Rigid reinforcing rods 28 are placed inside the hollow cylindrical foam reinforcing 30 through a slit along the length of the cylindrical foam reinforcing 30 or through the hollow in the center of the foam reinforcing 30. Rigid reinforcing rods 28 provide limb splint 36 the strength to resist bending of the limb at the elbow or knee. Rigid reinforcing rods 28 keep the limb fully or partially extended.

It is preferred that the rigid reinforcing rods 28 be made of low temperature thermal plastic, however, the rigid reinforcing rods 28 may be made of other plastic, metal or composite material that facilitates molding to a patient's angle of limb extension. The rigid reinforcing rod 28 should be made a sufficient thickness to support the limb extension of a patient depending on the patient's size, strength, and reinforcing material chosen.

Hollow cylindrical foam reinforcing 30 is used as a protective padding to prohibit the rigid reinforcing rod 28 from irritating the patient's skin and causing skin break down. Hollow cylindrical foam reinforcing 30 is made of cross-link polyethylene foam with a thickness of at least 1.27 cm. However, it could also be made of 0.64 cm. thick cross-link polyethylene sheet rolled several times about the rigid reinforcing rod 28 to a minimum thickness of 1.27 cm. and secured with adhesive tape.

After surrounding the rigid reinforcing rod 28 with the hollow foam reinforcing 30, insert them into the limb splint 36 pockets 42 as shown in FIGS. 3, 4, 7 and secure with the hook and loop fastened seam 40.

Figure 2:
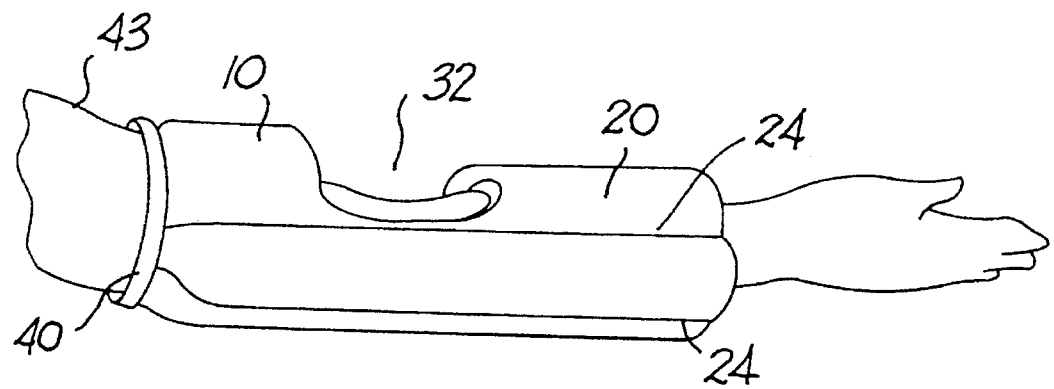
FIG. 2 is an illustration of the left side view of the modified limb splint and restraint device worn on a fully extended arm.

Finally, the splint 36 is folded about the limb in a generally tubular form as shown in FIGS. 1 and 2. The foam padded semi-circular extended openings 32 with their hook and loop fasteners 26 as shown in FIGS. 3, 4, 6, and 8, are secured where they form a generally circular opening at the inside of the elbow or behind the knee. These are the locations where skin break down occurs to patients who keep their limbs flexed. The pockets 42, holding the reinforcing members, surround the rest of the limb and support limb extension. It must be noted that the rigid reinforcing rod 28 of the modified limb splint 36 must be removed prior to washing.

CONCLUSION, RAMIFICATIONS AND SCOPE OF INVENTION

Thus the reader will see the limb splint provides structural resistance to limb extension by utilizing a series of elongated resilient reinforcing members situated parallel to the length of the limb around the limb. It allows air flow between the limb and splint. It is made of soft ,absorbing, non-allergenic and machine launderable fabric covered resilient reinforcing members. It allows the removal and replacement of its reinforcing members without necessitating the total discarding of the whole limb splint. It provides a comfortable restraint for patients who tend to bite their hands and arms or hit themselves. It combines an inexpensive process and relatively inexpensive materials into a limb splint. It allows for a modification to provide openings at the inside of elbows or at the backside of knees that give pain relief and healing to those patients who have skin ulcerations at these locations while maintaining limb extension. Finally, it can be modified to use fully padded rigid reinforcing members that mold to the patient's greatest angle of limb extension should they not be able to attain full extension.

While the above description contains many specifications, these should not be construed as limitations on the scope of the invention, but rather as an exemplification of one preferred embodiment thereof. Many other variations are possible. For example, the opening could be placed anywhere besides the inside of the elbow or behind the knee, or more than one opening could be provided for in the limb splint, or the limb splint could be any other shape than a rectangle, or the reinforcing members could have a non-circular cross section. Accordingly, the scope of the invention should be determined not by the embodiments illustrated, but by the appended claims and their legal equivalents.

I claim:

1. A splint device adapted to be rolled into a tubular shape having a longitudinal central axis about the limb of a user, said device comprising:

a covering having a pair of opposite ends and a first fastener mechanism for releasably securing said opposite ends together to form said tubular shape about a user's limb, said covering having a plurality of spaced pockets running substantially parallel to said longitudinal central axis of said tubular shape, each of said spaced pockets having an opening along one side of said device for receiving a reinforcing member;

said reinforcing members positioned within said pockets having a shape that together with said covering define a plurality of parallel cylinders having tangential lines of contact with a user's skin, said parallel cylinders forming a plurality of channels lying between said tangential lines of contact and running along an inside surface of said tubular shape and substantially parallel to said longitudinal axis thereby permitting flow of air between the device and the user's limb along said channels when said device is wrapped around the user's limb; and a second fastener mechanism forming a seam along said one side of said covering between said two ends and releasably closing said openings to permit removal of said reinforcing members.

2. The device of claim 1 including a rigid rod releasably encased by each of said reinforcing members.

3. The device of claim 2 in which said reinforcing members are made from a foamed material.

4. The device of claim 1 in which said second fastening mechanism opens and closes said one side thereby providing access to all of said pockets simultaneously.

5. The device of claim 1 in which each of said ends defines an arcuate edge such that when said device is formed into the tubular shape about a user's limb the arcuate edges form an opening in said device thereby providing access to skin of the user's limb.

6. The device of claim 5 in which said arcuate edges are each positioned between a pair of reinforcing elements having substantially flat surfaces and said first fastening mechanism comprises a hook and loop fastener secured to the covering over said reinforcing elements.

\* \* \* \* \*